(12) United States Patent
Ramirez

(10) Patent No.: US 8,772,568 B1
(45) Date of Patent: Jul. 8, 2014

(54) INCONTINENCE DETECTION SYSTEM

(71) Applicant: Fanny Ramirez, La Quinta, CA (US)

(72) Inventor: Fanny Ramirez, La Quinta, CA (US)

( * ) Notice: Subject to any disclaimer, the term of this patent is extended or adjusted under 35 U.S.C. 154(b) by 0 days.

(21) Appl. No.: 13/936,026

(22) Filed: Jul. 5, 2013

(51) Int. Cl.
*A61F 13/42* (2006.01)

(52) U.S. Cl.
CPC ..................................... *A61F 13/42* (2013.01)
USPC ......................................................... 604/361

(58) Field of Classification Search
CPC ........................... A61F 13/42; A61F 2013/424
USPC .................. 604/361, 388, 393–396, 401, 402
See application file for complete search history.

(56) References Cited

U.S. PATENT DOCUMENTS

| | | | | |
|---|---|---|---|---|
| 4,356,818 A | * | 11/1982 | Macias et al. | 128/886 |
| 5,838,240 A | * | 11/1998 | Johnson | 340/604 |
| 6,200,250 B1 | * | 3/2001 | Janszen | 493/383 |
| 6,246,330 B1 | * | 6/2001 | Nielsen | 340/604 |
| D455,000 S | * | 4/2002 | Williams | D2/700 |
| 6,559,772 B2 | * | 5/2003 | Zand et al. | 340/604 |
| 7,195,622 B2 | * | 3/2007 | Lindstrom | 604/392 |
| 7,250,547 B1 | * | 7/2007 | Hofmeister et al. | 604/361 |
| 2002/0135489 A1 | * | 9/2002 | Chen et al. | 340/604 |
| 2004/0147888 A1 | * | 7/2004 | Huang et al. | 604/361 |
| 2007/0270774 A1 | * | 11/2007 | Bergman et al. | 604/361 |
| 2008/0266117 A1 | * | 10/2008 | Song et al. | 340/573.5 |
| 2010/0152688 A1 | * | 6/2010 | Handwerker et al. | 604/361 |
| 2012/0206265 A1 | * | 8/2012 | Solazzo et al. | 340/573.5 |

* cited by examiner

*Primary Examiner* — (Jackie) Tan-Uyen T Ho
*Assistant Examiner* — Kathryn E Ditmer
(74) *Attorney, Agent, or Firm* — Plager Schack LLP

(57) ABSTRACT

A system for detecting incontinence is configured to discern when a patient has eliminated and communicate a signal to a control center. The system includes an undergarment that is sufficiently sized to be worn around a waist of the patient. A disposable sensor assembly is mechanically coupled to the undergarment. The disposable sensor assembly can transmit the signal when the patient has eliminated. A wireless transmitter is communicatively coupled to the disposable sensor assembly which receives the signal from the disposable sensor assembly and communicates the signal. A wireless receiver is communicatively coupled to the wireless transmitter which receivers the signal and communicates the signal to the control center. In this manner, personnel in the control center can treat the patient upon receipt of the signal.

9 Claims, 3 Drawing Sheets

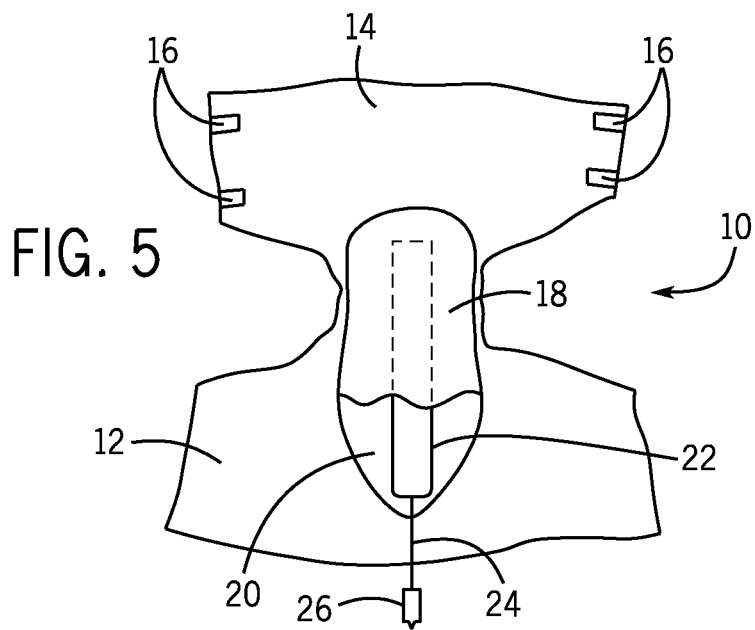
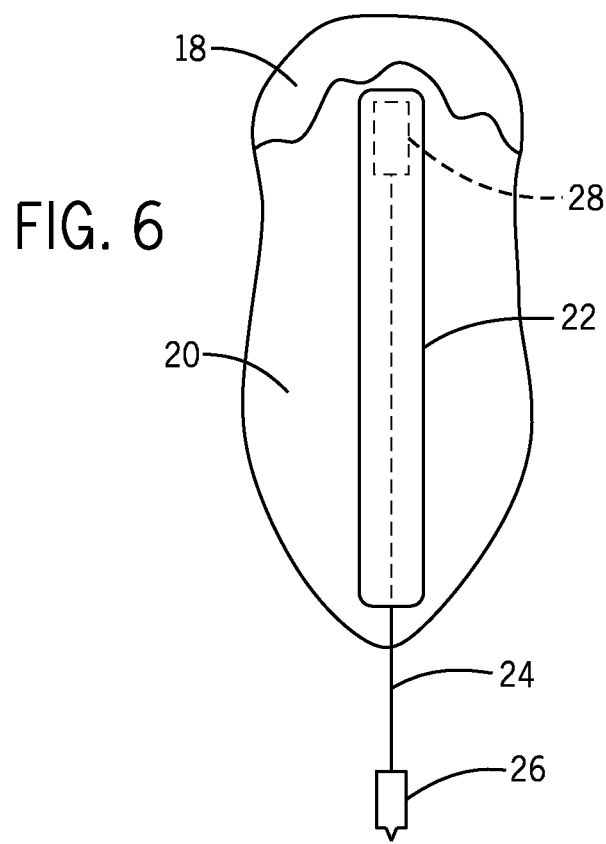

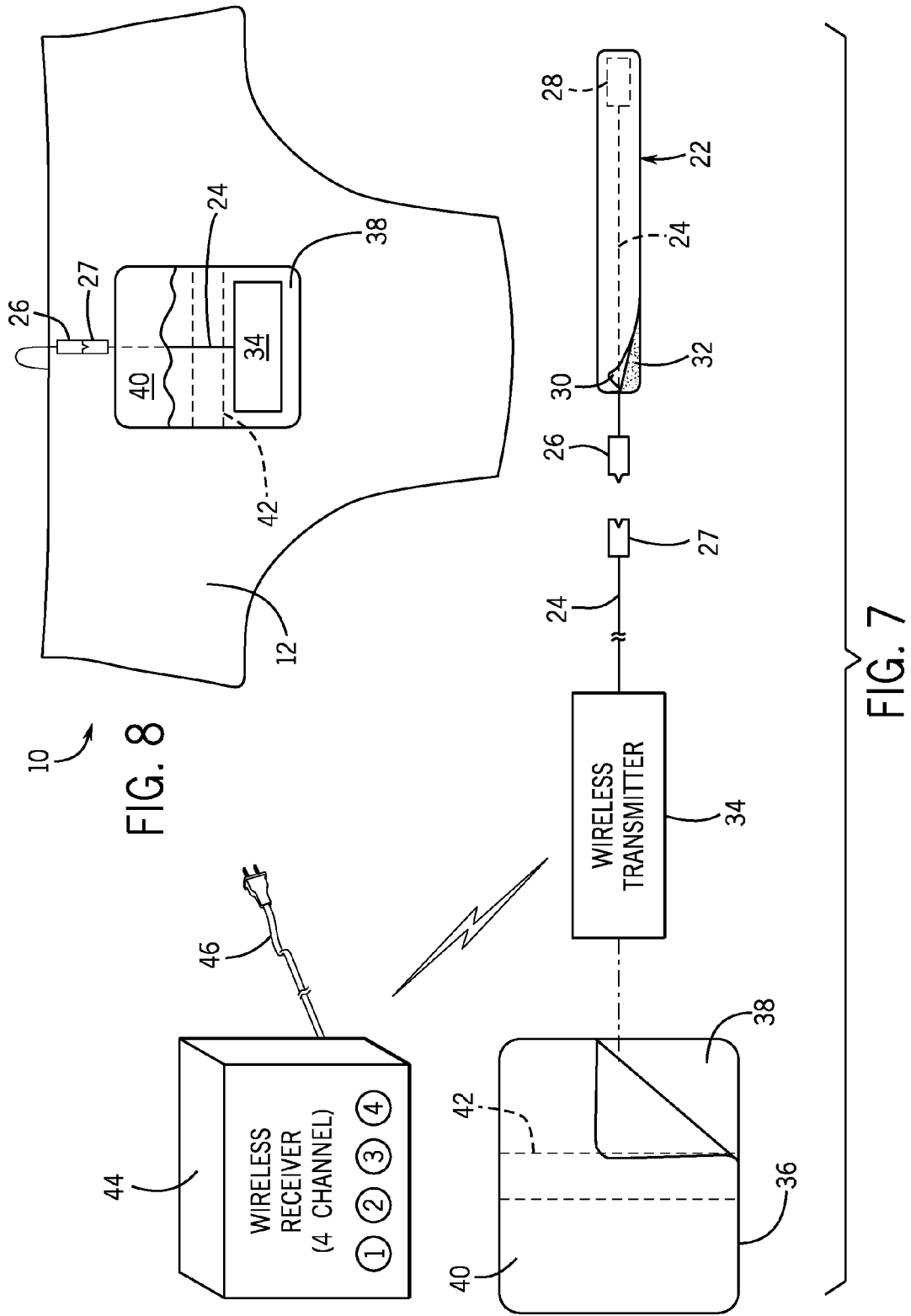

INCONTINENCE DETECTION SYSTEM

BACKGROUND

The embodiments herein relate generally to systems utilized to detect incontinence and then communicate incidents of incontinence.

SUMMARY

A system for detecting incontinence is configured to discern when a patient has eliminated and communicate a signal to a control center. The system includes an undergarment that is sufficiently sized to be worn around a waist of the patient. A disposable sensor assembly is mechanically coupled to the undergarment. The disposable sensor assembly can transmit the signal when the patient has eliminated. A wireless transmitter is communicatively coupled to the disposable sensor assembly which receives the signal from the disposable sensor assembly and communicates the signal. A wireless receiver is communicatively coupled to the wireless transmitter which receivers the signal and communicates the signal to the control center. In this manner, personnel in the control center can treat the patient upon receipt of the signal.

In some embodiments, the undergarment also includes a first panel mechanically coupled to a second panel. The second panel mechanically coupled to adhesive tabs. In this manner, the adhesive tabs can be used to mechanically couple the first panel to the second panel to create a removable couple that can seal the undergarment around the patient. The undergarment also includes a first absorbent layer mechanically coupled to a second absorbent layer such that a space between the two absorbent layers can accommodate the disposable sensor assembly.

In some embodiments, the disposable sensor assembly comprises a male connector electrically coupled to a sensor with a wire. The wireless transmitter is electrically coupled to a wire which is further electrically coupled to a female connector that can be electrically coupled to the male connector.

In some embodiments a pouch is mechanically coupled to the undergarment. The pouch further comprises a first pouch layer detachably coupled to a second pouch layer with a hook and loop fastener. In this manner, the pouch can accommodate the wireless transmitter.

In some embodiments, the undergarment is mechanically coupled to an elastic waistband. This assists patients who are bed bound, in hospice care, in a hospital, in residential care or are personally caring for themselves.

In some embodiments, the undergarment is mechanically coupled to an elastic waistband and adhesive tabs. This can be useful for patients who are capable of walking.

In some embodiments, the undergarment is mechanically coupled to a belt. This can be useful for patients who are capable of walking.

In some embodiments, the undergarment comprises a front portion mechanically coupled to a lower portion by a belt. A first strap and a second strap are further mechanically coupled to the front portion wherein each strap can fit over a shoulder of the patient. Each strap is further mechanically coupled to a strap attachment which can bind each strap to the belt.

BRIEF DESCRIPTION OF THE FIGURES

The detailed description of some embodiments of the invention is made below with reference to the accompanying figures, wherein like numerals represent corresponding parts of the figures.

FIG. 5 is a front elevation view with parts broken away, showing the garment in an open position.

FIG. 6 is a detail front elevation view with parts broken away.

FIG. 7 is a schematic diagram.

FIG. 8 is a front elevation view showing the garment in a folded position.

DETAILED DESCRIPTION OF CERTAIN EMBODIMENTS

Figure 1:
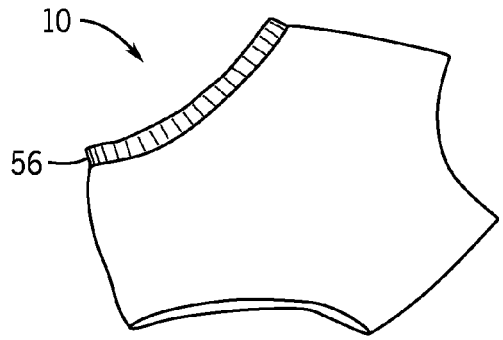
FIG. 1 is a perspective view of an embodiment of the invention.

Every patient's situation is different and different configurations of undergarments can be tailored to assist different patients. By way of example and referring to FIG. 1, a first configuration is shown where undergarment 10 is mechanically coupled to elastic waistband 56. This is useful for patients who are bed bound, in hospice care, in a hospital, in residential care or are personally caring for themselves.

Figure 2:
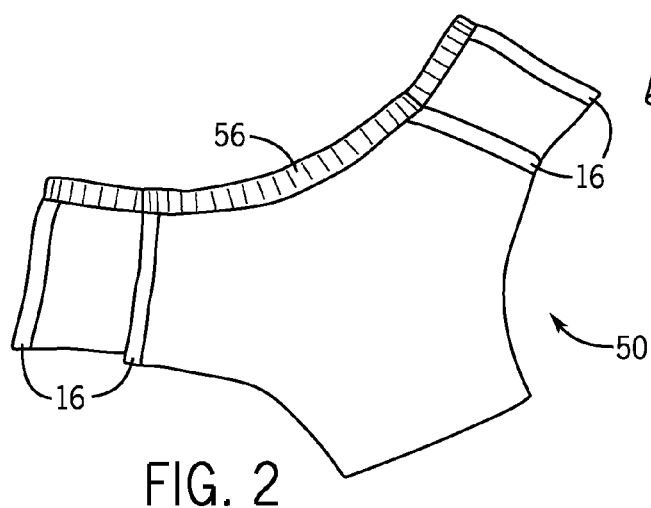
FIG. 2 is a front perspective view of a second configuration of the invention.

By way of example and referring to FIG. 2, a second configuration is shown where undergarment 56 is mechanically coupled to elastic waistband 56 and adhesive tabs 16. This can be useful for patients who are capable of walking and need a stronger upper seal to hold first panel 12 to second panel 14.

Figure 3:
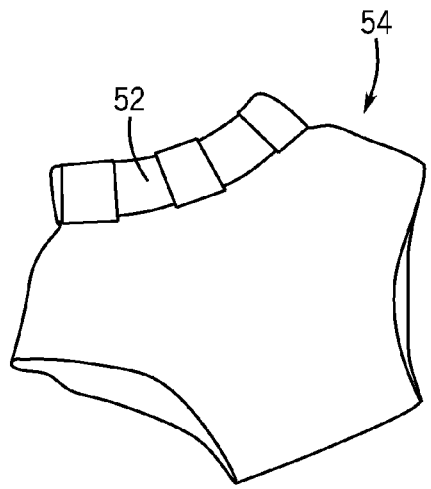
FIG. 3 is a front perspective view of a third configuration of the invention.

By way of example and referring to FIG. 3, a third configuration is shown where undergarment 54 is mechanically coupled to belt 52. Like the second configuration, the third configuration is appropriate for ambulatory patients. The two designs differ to accommodate the dexterity of the patient. Some patients struggle with undoing a belt, but can handle adhesives well. Other patients struggle with adhesives, but can handle a belt.

Figure 4A:
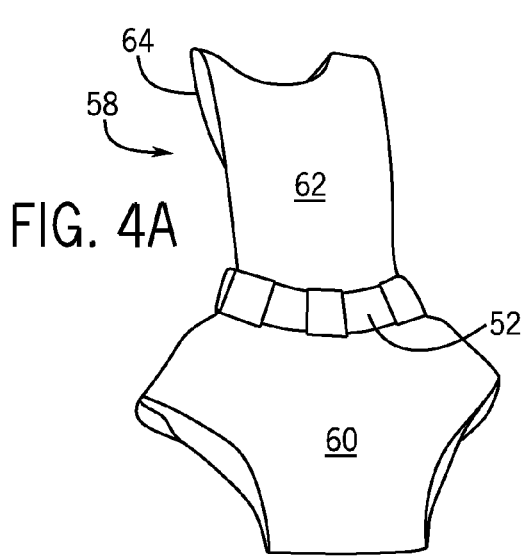
FIG. 4A is a front perspective view of fourth configuration of the invention.
Figure 4B:
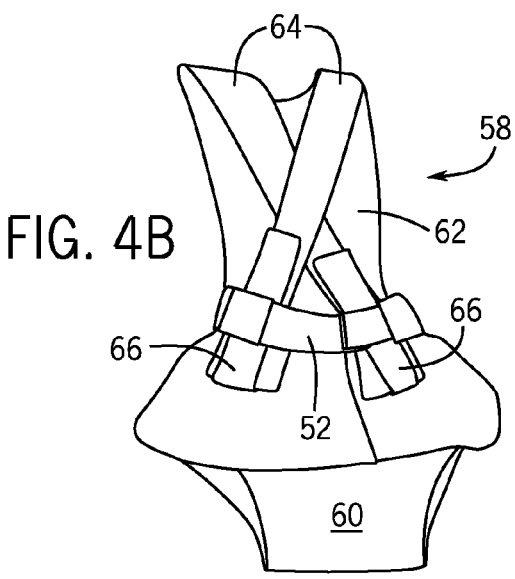
FIG. 4B is a rear perspective view of the fourth configuration.

By way of example and referring to FIGS. 4A and 4B, a fourth configuration is shown where undergarment 58 comprises front portion 62 mechanically coupled to lower portion 60 by belt 52. Front portion 62 is further mechanically coupled to first strap 64 and second strap 64 where each strap 64 can fit over a shoulder of a patient. Each strap 64 is further mechanically coupled to strap attachment 66 which can wrap around and bind straps 64 to belt 52. This configuration is useful for patients with dementia or another condition where the patient attempts to remove ones clothes, which can cause a mess. The patient will likely be unable to reach and undo the straps to remove undergarment 58.

By way of example, and referring to FIG. 5, FIG. 6, FIG. 7 and FIG. 8, one embodiment of the present system includes undergarment 10. Undergarment 10 comprises first panel 12 mechanically coupled to second panel 14. Second panel 14 is mechanically coupled to adhesive tabs 16. Adhesive tabs 16 can be used to mechanically couple first panel 12 to second panel 14 to create a removable couple that can seal undergarment 10 around a patient in a variety of manners as shown in FIG. 1, FIG. 2, FIG. 3 and FIG. 4 above.

In a central portion of undergarment 10 first absorbent layer 18 is mechanically coupled to second absorbent layer 20 in a space between the two absorbent layers is disposable sensor assembly 22. Disposable sensor assembly 22 comprises male connector 26 electrically coupled to sensor 28 with wire 24.

Turning to FIG. 8, male connector 26 is mechanically and electrically coupled to female connector 27. Female connector 27 is electrically coupled to transmitter 34 with wire 24. Practically, undergarment 10 can be mechanically coupled to pouch 36. Pouch 36 comprises first pouch layer 38 detachably coupled to second pouch layer 40 with hook and loop fastener 42. In other embodiments, any efficient detachable couple could be used such a buttons, snaps, resealable adhesives and so on.

To assemble undergarment 10, a user can utilize an undergarment with disposable sensor assembly 22 already installed or a user can install disposable sensor assembly 22 in an existing undergarment. To do the latter, as shown in FIG. 7, disposable sensor assembly 22 should come mechanically coupled to adhesive layer 32 which can be covered by adhesive covering 30. A user would remove adhesive covering 30 to expose adhesive 32 which could be placed between first absorbent layer 18 and second absorbent layer 20.

Sensor 28 is configured to detect and transmit a signal upon the introduction of solid or liquid waste to sensor 28. Disposable sensor assembly 22 is designed for a single use. However wireless transmitter 34 can be reused a number of times. Wireless transmitter 34 is communicatively coupled to wireless receiver 44 which is electrically coupled to a power source with cord 46. Each wireless transmitter 34 used in an area is coded with a unique signal to coordinate with wireless receiver 44. For instance, a first wireless transmitter 34 used on a first patient is communicatively coupled to a first channel on wireless receiver 44. Similarly, a second wireless transmitter 34 used on a second patient is communicatively coupled to a second channel on wireless receiver 44. Likewise, a third wireless transmitter 34 used on a third patient is communicatively coupled to a third channel on wireless receiver 44. Additionally, a fourth wireless transmitter 34 used on a fourth patient is communicatively coupled to a fourth channel on wireless receiver 44. Essentially, when a patient eliminates, a signal will be sent to a control center such as a nurse's station wherein personnel will know that the patient needs to have undergarment 10 replaced.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. A system for detecting incontinence configured to discern when a patient has eliminated and to communicate a signal to a control center; the system comprising:
   an undergarment sufficiently sized to be worn around a waist of the patient having a first absorbent layer and a second absorbent layer;
   a pouch mechanically coupled to the undergarment;
   a disposable sensor assembly configured to be mechanically coupled to the undergarment, comprising an adhesive layer covered by an adhesive covering wherein the adhesive covering is removed to expose the adhesive to be placed between the first absorbent layer and the second absorbent layer; wherein the disposable sensor assembly can transmit the signal when the patient has eliminated;
   a wireless transmitter inserted into the pouch and communicatively coupled to the disposable sensor assembly, which receives the signal from the disposable sensor assembly and communicates the signal;
   a wireless receiver communicatively coupled to the wireless transmitter which receivers the signal and communicates the signal to the control center;
   wherein personnel in the control center can treat the patient upon receipt of the signal.

2. The system of claim 1, wherein the undergarment further comprises:
   a first panel mechanically coupled to a second panel;
   the second panel mechanically coupled to adhesive tabs;
   wherein the adhesive tabs can be used to mechanically couple the first panel to the second panel to create a removable couple that can seal the undergarment around the patient.

3. The system of claim 1, wherein the first absorbent layer is mechanically coupled to the second absorbent layer such that a space between the two absorbent layers can accommodate the disposable sensor assembly.

4. The system of claim 1, wherein the disposable sensor assembly comprises a male connector electrically coupled to a sensor with a wire.

5. The system of claim 1, wherein the pouch further comprises a first pouch layer detachably coupled to a second pouch layer with a hook and loop fastener.

6. The system of claim 1, wherein the undergarment is mechanically coupled to an elastic waistband to assist patients who are bed bound, in hospice care, in a hospital, in residential care or are personally caring for themselves.

7. The system of claim 1, wherein the undergarment is mechanically coupled to an elastic waistband and adhesive tabs.

8. The system of claim 1, wherein the undergarment is mechanically coupled to a belt.

9. The system of claim 1, wherein the undergarment further comprises;
   a front portion mechanically coupled to a lower portion by a belt;
   a first strap and a second strap further mechanically coupled to the front portion wherein each strap can fit over a shoulder of the patient;
   wherein each strap is further mechanically coupled to a strap attachment to bind each strap to the belt.

\* \* \* \* \*